(12) United States Patent
Henriksson

(10) Patent No.: US 8,475,712 B2
(45) Date of Patent: Jul. 2, 2013

(54) ARRANGEMENT FOR NEUTRALISATION OR MICROORGANISMS

(75) Inventor: Par H Henriksson, Lund (SE)

(73) Assignee: Arc Aroma Pure AB, Lund (SE)

( * ) Notice: Subject to any disclaimer, the term of this patent is extended or adjusted under 35 U.S.C. 154(b) by 276 days.

(21) Appl. No.: 12/936,437

(22) PCT Filed: Mar. 30, 2009

(86) PCT No.: PCT/SE2009/000164
§ 371 (c)(1),
(2), (4) Date: Oct. 5, 2010

(87) PCT Pub. No.: WO2009/126084
PCT Pub. Date: Oct. 15, 2009

(65) Prior Publication Data
US 2011/0033591 A1    Feb. 10, 2011

(30) Foreign Application Priority Data
Apr. 7, 2008   (SE) ...................................... 0800771

(51) Int. Cl.
*A61L 2/00*    (2006.01)
*B01J 19/00*   (2006.01)
*G03G 15/02*   (2006.01)
*H05F 3/00*    (2006.01)
*B05B 5/053*   (2006.01)
*F16K 15/20*   (2006.01)

(52) U.S. Cl.
USPC .............. 422/22; 422/23; 422/291; 361/225; 361/226; 137/825; 137/826

(58) Field of Classification Search
USPC . 422/22, 24, 23, 291; 361/225, 226; 137/825, 137/826
See application file for complete search history.

(56) References Cited

U.S. PATENT DOCUMENTS 5,098,377 A * 3/1992 Borsanyi et al. ................ 604/30
5,235,905 A   8/1993 Bushnell et al.
(Continued)

FOREIGN PATENT DOCUMENTS
WO       99/50185 A1    10/1999

OTHER PUBLICATIONS
International Report on Patentability.
(Continued)

*Primary Examiner* — Regina M Yoo
(74) *Attorney, Agent, or Firm* — Ladas & Parry LLP

(57) ABSTRACT

An arrangement for the exposure of a pumpable medium to an electric field. The arrangement comprises, at least two power supplies (100) for the generation of electrical voltage, at least one non-conducting chamber (102) for pumping said pumpable medium, which said at least one chamber (102) is provided with a first (106) and a second electrode plate (108), a control means (104) for controlling said at least two power supplies (100). During control the control means (104), by synchronous control, establishes a series connection between at least two of said at least two power supplies (100), the first electrode plate (106) and the second electrode plate (108). A resulting composite voltage arises between the first (106) and the second electrode plate (108), which resulting composite voltage will result in an electric field between the first (106) and the second electrode plate (108). The pumpable medium is exposed to the electric field. A method for the exposure of a pumpable medium to an electric field is also provided.

37 Claims, 4 Drawing Sheets

U.S. PATENT DOCUMENTS

| | | | |
|---|---|---|---|
| 6,110,423 | A | 8/2000 | Bushnell et al. |
| 6,623,964 | B2 | 9/2003 | Vernhes et al. |
| 7,616,528 | B2 * | 11/2009 | Meadows .................. 368/76 |
| 2004/0112840 | A1 | 6/2004 | Bourazak et al. |
| 2005/0008740 | A1 | 1/2005 | Lindgren |
| 2008/0143260 | A1 * | 6/2008 | Tuymer et al. ........... 315/111.21 |
| 2009/0201620 | A1 * | 8/2009 | Gray et al. .................... 361/159 |
| 2010/0119879 | A1 * | 5/2010 | Girguis et al. .................... 429/2 |
| 2012/0097201 | A1 * | 4/2012 | Field .......................... 134/58 R |

OTHER PUBLICATIONS

European Search Report dated Jun. 13, 2012 Appln. No. 09730423. 2-2104 /2262739 PCT/SE2009000164.

International Search Report: PCT/SE2009/000164.

* cited by examiner

ARRANGEMENT FOR NEUTRALISATION OR MICROORGANISMS

TECHNICAL FIELD

The present invention relates to an arrangement for the exposure of a pumpable medium to an electric field. The invention also concerns a method as performed expose a pumpable medium for an electric field. The invention relates also to a number of applications of the said arrangement.

TECHNICAL BACKGROUND

To destroy or inactivate harmful microorganisms in different types of fluids are today common in most application areas. For example, most liquid foodstuffs are exposed to one or more process steps that are designed to destroy unwanted microorganisms and thus extend the shelf life of the product. Similarly, different processes are used for purifying different kinds of contaminated water alternatively sludge, petroleum products or other pumpable products.

A common method for food treatment is so-called pasteurization. During pasteurization the food in question is heated for a short period of time to a temperature which is high enough to inactivate the microorganisms that possibly are present in the food. When the food is heated during pasteurization, however, its taste and chemical composition may change due to the increase in temperature.

Another disadvantage with pasteurization is that a large amount of energy is needed to heat the food, and then cooling it to a suitable storage temperature. Energy consumption is currently related to high costs that ultimately results in an increase in the cost of the processed food.

In the case where different kind of water is purified to achieve a higher water quality several treatment methods are used, this includes treatment with chemicals, biological methods, UV light or ozone gas. These methods are however, costly and often require the use of additional methods to achieve the desired end-result.

Another option to deactivate microorganisms in fluids is to expose the liquid in case to an electric field.

A known method is based on a tube which has been provided with electrodes, between which an electrical voltage is applied. When a liquid or similar flows passing the electrodes, the liquid will be subjected to an electric field. In this case, however, it is difficult to control the extent of the treatment, this since the electric field the field strength is difficult to predict. Furthermore, the liquid flow velocity will differ at different location over the intersection of the tube, leading to an uneven treatment.

SE-520 666 C2 describes a method and an arrangement where a pumpable substance is exposed to an electric field. When the method is performed, the pumpable substance is first brought into the electric field, after which it is exposed to the electric field. Finally the pumpable substance is brought out from the electric field. While the substance is exposed to the electric field, at least one volume is separated which is moved during the exposure to the electric field. The above arrangement for the treatment of a pumpable substance using an electric field includes a container in which the pump only substance can be accommodated. The arrangement also includes a source for the generation of the electric field, and at least a separated space in which the pumpable can be accommodated and subjected to the electric field. When the above method and arrangement is used a significant risk that the previously treated pumpable substance is contaminated in case something fails. This risk exists because no measurement is performed where the actual electric field is ensured during the exposure. Would therefore not properly treated pumpable substance be carried forward after treatment, then the previously treated substance is contaminated. Furthermore, there are no organs to ensure that no air or gas bubbles are present in the substance being treated or that the substance can be pressurized to minimize the risk of air-filled cavities in the treated substance.

SUMMARY OF THE INVENTION

One purpose of the present invention is to eliminate or at least mitigate the above disadvantages and to provide an improved arrangement and an improved method for the neutralization of microorganisms in a pumpable medium by exposing the medium to an electric field.

This and other purposes and advantages will be apparent from the following description of the present invention. Preferred arrangements are described in the dependent patent claims.

Consequently, an arrangement is provided for the exposure of a pumpable medium to an electric field. The arrangement comprises:

at least two power supplies for the generation of an electrical voltage;

at least one non-conducting chamber for pumping said pumpable medium, which said at least one chamber is provided with a first and a second electrode plate;

a control means for controlling said at least two power supplies. The control means prepares synchronously a short duration serial connection between at least two of said at least two power supplies, the first electrode plate and the second electrode plate at activation. A resulting composite voltage will appear between the first and second electrode plate, said resulting composite voltage will create an electric field between the first and second electrode plate. The pumpable medium is exposed to the electric field.

The arrangement according to this invention is advantageous in that it in a controlled manner exposes the pumpable medium to an electric field. By generating the resulting composite voltage using a short duration serial connection of a number of power supplies, power supplies based on low cost standard components can be used.

The field strength of the electrical field of the arrangement between the first and second electrode plate can be in a range of for example 1-30 kV/cm. This can be advantageous as the field can be adapted to destroy various types of microorganisms that require different field strength for the deactivation.

The arrangements said each power supply can provide an adjustable voltage in the range of, for example, 230-2000 volts, which can be advantageous because the short duration resulting composite voltage can be adjusted very easily. It should recognized that it would be possible that each said power supply under the present invention could provide an adjustable voltage which is higher than the above specified range, such as up to 3000 volts, and also somewhat higher. In this regard it is the existing component technology and which components that are available on the market that sets the limit and therefore not the present invention. In other words, a voltage in the range of 230-3000 volts is fully possible under the present invention.

Said power supply of the arrangement may comprise a voltage converter, a charge storing element and a switch, using which a simple and functional power supply can be achieved by the use of low cost standard components.

The voltage converter of said arrangement may be a transformer, which can be advantageous because transformers are commonly used and inexpensive standard components.

The charge storing element of said arrangement can be at least one capacitor, which enables that the charge storing element can be achieved by using standard components.

The switch of said arrangement can be an electrically insulating body, which may be advantageous in that no electrical connection exist between switch and the controller.

The switch of said arrangement can be an optical coupler, which enables that a serial connection of the power supplies can be established with a short duration and with a very short time delay.

Said control means of the arrangement can synchronously establish a series connection between at least two of said at least two power supplies, the first electrode plate and the second electrode plate by synchronous control of each power supply switch. This means that a resulting composite voltage with a short duration can be generated in a simple manner.

Said at least two power supply switches of the arrangement can be controlled by a common control signal, which can be advantageous since a series connection can be established synchronously in a simple manner.

Said control means of the arrangement can be arranged to generate a control signal in the form of a pulse with a duration of for example 1-100 microseconds, which means that the resulting composite voltage duration can be controlled.

Said control means of the arrangement can be arranged to repeat the pulse with a selectable number of pulses, such as 1 to 100 pulses with a frequency of for example 1 Hz-100 kHz. This enables that the pumpable medium can be exposed to an electric field several times in a simple manner.

Said control means of the arrangement can be arranged to detect errors in each of power supply before and/or during the series connection is performed. These errors can, for example, be selected from the group consisting of, component failure, pump failure, voltage at the output of power supply, short circuit of the said switches, leakage currents in said charge storing element and voltage losses in said voltage converter. This may be advantageous as during a fault condition indication it can be avoided to establish a serial connection and thereby damaging other functional components of the arrangement.

Said control means of the arrangement can be arranged to measure the electrical properties, between the first and second electrode plate. The electrical properties may include but are not limited to resistance, impedance, capacitance and inductance. The resulting composite voltage can be adjusted so that a predetermined field strength achieved between the first and second electrode plate. This can be advantageous in that the resulting composite voltage can be adjusted to achieve a field strength that is sufficient to destroy the microorganisms present in the pumpable medium.

Said control means of the arrangement can apply a resulting composite voltage with a predetermined value between the first and second electrode plate and measure the time constant of the pulse and the amplitude of the voltage and current in the resulting field, after which the control means is able to adapt the resulting composite voltage so that a predetermined field strength achieved between the first and second electrode plate, when a resulting composite voltage is again applied. Also this can be advantageous in that the resulting composite voltage can be adjusted to achieve a field strength that is sufficient to destroy microorganisms present in the pumpable medium.

Said control means of the arrangement can control how many of the mentioned at least two power supplies that should be connected in serial and contribute to the resulting composite voltage. This means that the amplitude of the resulting composite voltage can be controlled in a simple and effective way.

The said at least one chamber of the arrangement can be an over-pressure pump that is connected to a feeding inlet pipe and discharge outlet pipe, which means that the risk of air existing in the chamber when the electric field is applied can be eliminated.

Said over-pressure pump of the arrangement may be a piston pump with a piston whose upper part forms one of the electrode plates. This can be advantageous because the electrode plates can be easily integrated into a standard pump device.

Said feeding inlet pipe of the arrangement can be provided with an inlet valve and/or said discharge outlet pipe of the arrangement can be equipped with an outlet valve, which means that it may be possible that in a controlled way control the inlet and outlet of the pumpable medium in the chamber.

The at least one said chamber of the arrangement can be fitted with a valve which allows the gaseous medium to pass through but prevents liquid medium and solid medium to pass. This can be advantageous because it may be important to ensure that no air is present in the chamber when the electrical field is applied.

The at least said one chamber of the arrangement can be fitted with a pressure transducer. The control means may be arranged not to establish a series connection of said at least two power supplies if a predetermined pressure is not recorded by the pressure transducer. Also this implies that it may be possible to ensure that no air is present in the chamber when the electrical field is applied.

The said at least one chamber of the arrangement can be fitted with a drain connection and a drainage valve. This allows that the pumpable medium may be discarded or returned before or after the exposure to the electric field.

The at least one chamber of the arrangement or the inlet feed tube and/or discharge outlet pipe can be fitted/equipped with an additive connection and an additive valve. This can be advantageous in that the additives in the form of catalysts, salts or the like can be added to the pumpable medium.

The distance between the arrangements first electrode plate and the arrangements second electrode plate may be less further from a centre point of the chamber than that closer to the centre point, which means that it may be possible to compensate for the peripheral effects of the electric field.

The first electrode plate of the arrangement and/or the second electrode plate of the arrangement may comprise non-conducting areas. Said non-conducting areas can be wider closer to a centre point of the chamber than that further from said centre point. Also this allows that it may be possible to compensate for the peripheral effects of the electric field.

The said at least one chamber of the arrangement can be an over pressure pump that is connected in parallel with at least one other chamber, which can also be an over pressure pump. This can be advantageous in that capacity could be increased in a simple manner.

The arrangement can be provided with a distributing means that controls the filling and the discharge of the pumpable medium to each chamber. This allows that a continuous flow of the pumpable medium can be achieved.

The method to expose a pumpable medium to an electric field, comprises the steps of;

to fill a chamber, having a first and a second electrode plate, with the pumpable medium;

to compress the pumpable medium to a predetermined pressure;

to vent air out from the pumpable medium through a valve;

to generate an electric voltage in at least two power supplies;

to establish a serial connection between the at least two mentioned power supplies, the first electrode plate and the second electrode plate, which resulting composite voltage expose the pumpable medium to an electric field;

to empty said chamber from the pumpable medium;

The method according to this invention is advantageous in that it in a controlled manner expose the pumpable medium to an electric field.

The method step to fill a chamber can further comprise exposing the pumpable medium to a pressure, which allows that it may be possible to evacuate any air or gas contained from the pumpable medium.

The method step to generate an electrical voltage and to establish a series connection can be performed several times in the mentioned order. This implies that the pumpable medium can be exposed to an electric field several times in a simple manner.

The method step to empty said chamber from the pumpable medium can also comprise to discharge said medium through a drainage valve. In this way, the pumpable medium is either discarded or returned before or after the exposure to the electric field.

The methods said at least one chamber can be connected in parallel with at least one other similar chamber and a distribution means can be arranged to control each chambers filling and discharge of pumpable medium so that at least one chamber is always filled with medium and at least one chamber is emptied of the medium. This allows that a continuous flow of the pumpable medium can be achieved.

The use of the arrangement may be to expose the pumpable medium, in which there is a risk of unhealthy microorganisms, for an electric field. This may be advantageous as the microorganisms in the pumpable medium can be neutralized.

The use of the arrangement may be to expose the pumpable food stuff for an electric field. This may be advantageous as the microorganisms in the pumpable food stuff can be neutralized.

The use of the arrangement may be to expose the hazardous water, pool water, pond water, contaminated water, humidification water, drinking water and/or waste water to an electric field.

The use of the arrangement may be to expose a suspended product for an electric field. This may be advantageous as the microorganisms in contaminated soil or other suspended products can be neutralized.

The use of the arrangement may further be to expose a commodity aimed for biogas production, for example a sludge for an electric field. Such a sludge material can contain bacteria that must be neutralized safe. Another commodity that can be processed in accordance with the present invention is a petroleum product, such as crude oil.

The use of the arrangement may be to expose a pumpable pharmaceutical and/or a pumpable raw material for the manufacture of pharmaceutical to an electric field.

The use of the arrangement may be in conjunction to a mobile water treatment plant, in conjunction to a hot water tank, a humidification plant, a pool or a basin. This means that the risk that water-borne infections are transmitted can be eliminated in a simple manner.

The use of the arrangement may be combined with at least one treatment selected from the group consisting of, but not limited to, UV, ozone and vortex treatment with the aim to clean water. This means that purifying water treatment can be made more efficient in a simple and cost effective manner.

Other purposes, characteristics, advantages and described embodiments of the present invention are apparent from the following detailed description in connection with the drawings and the attached patent claims.

BRIEF DESCRIPTION OF DRAWINGS

Preferred embodiment of the present invention is described below with reference to the attached drawings.

DESCRIPTION OF PREFERRED EMBODIMENTS

Figure 1:
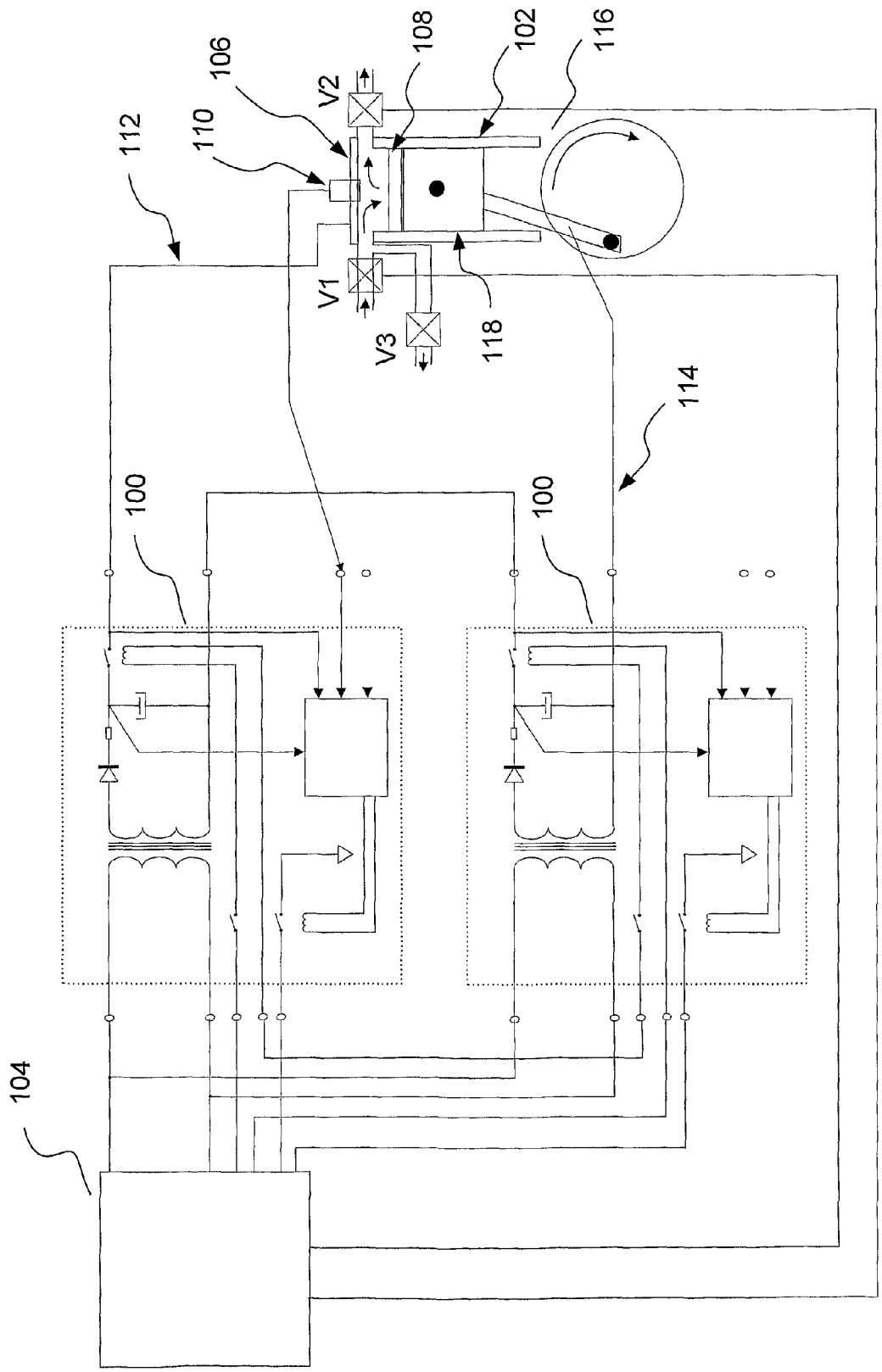
FIG. 1 is a schematic view of an arrangement according to a first embodiment of the present invention.
Figure 2:
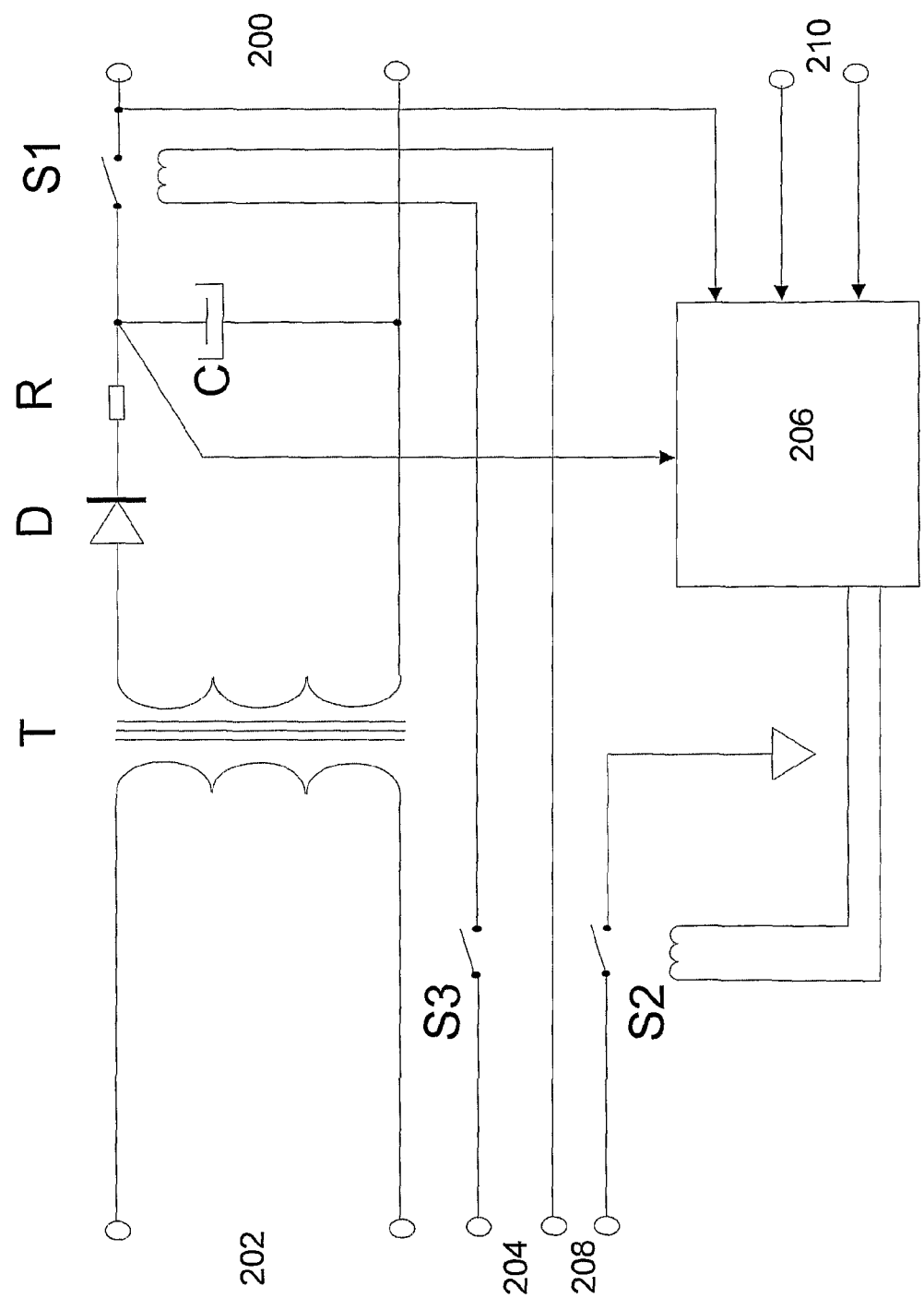
FIG. 2 is a schematic view of a power supply according to a first embodiment.

The arrangement in FIG. 1 includes two power supplies 100, which are shown in more detail in FIG. 2. Furthermore, the arrangement includes a non-conductive chamber 102 and a control means 104. The chamber 102 is equipped with a first electrode plate 106 and a second electrode plate 108. When the control means 104 establishes a serial connection between the two power supplies 100 a resulting composite voltage is produced between the first 106 and the second electrode plate 108. The resulting composite voltage will, when it is produced between the first 106 and the second electrode plate 108 generate an electrical field between electrode plates 106, 108. The resulting composite voltage is feed from the power supplies 100 to the first 106 and the second electrode plate 108 by means of electrical conductors 112, 114.

Since the purpose of the arrangement is to enable the exposure of the pumpable medium to an electric field to neutralize microorganisms, it is important that the field between the electrode plates 106, 108 reaches an appropriate level. The aim is that the electrical field must reach a level that is sufficient to fracture the cell membranes of the microorganisms to incapacitate the micro organisms. As the cell membrane of various micro organisms require different fields strength in order fracture the cell membrane an embodiment of the invention generates a field in the range 1-30 kV/cm, more preferably in the range 2-10 kV/cm.

The treatment when the pumpable medium is exposed to the electric field is repeated according an embodiment of this invention several times, preferably 1-100 times, more preferably 5-30 times.

The treatment is performed by a number of voltage pulses which give rise to the electric field. According to one embodiment the pulses are repeated with a pulse frequency in the interval 1 Hz-100 kHz or more preferred in the interval 0.5-100 kHz.

According to one embodiment each pulse has a duration preferably 1-100 micro seconds, or more preferred 2-10 micro seconds.

It is important to realize that, according to the invention is fully possible with higher frequencies than the above specified range, e.g. as high as up to 1 MHz when the pulse duration is e.g. about 1 microsecond. According to a specific embodiment of the present invention thus is the frequency in the range 1 Hz-1 MHz, as for instance in the range 1 Hz-100 kHz.

Furthermore, the pulse duration can be shorter than the above specified range, e.g. as short as 0.1 micro seconds and even shorter, which allows frequencies above 1 MHz. According to a specific embodiment of the present invention the pulse duration is in the range 0.1-100 microseconds, as in the range 1-100 microseconds.

When the pumpable medium is to be subjected to the electric field it is introduced through the inlet valve V1. In a similar manner it will be outlet through the exit valve V2 after it has been subjected to the electric field.

If the pumpable medium which has been exposed to the electric field for any reason is not to be pumped out by the outlet valve V2 it can instead according to a specific embodiment be released through the drain valve V3. Drain valve V3 has two main objectives. The first objective is that a pumpable medium that have already been subjected to an electric field can be discarded and placed in such as a sewage or a tank. In this way, it is possible to discard the parts of the pumpable medium which in any way presents with properties that make difficult or not possible to treat. The second main purpose of the drain valve V3 is that a pumpable medium that is located in the chamber can be brought back to the non-treated pumpable medium supply, to again be introduced into the chamber 102 via the inlet valve V2. To be able to perform this is particularly useful when the arrangement is activated during start-up and shall be evacuated from air before the electric field can be applied.

To be able to evacuate the system from air it is according to one embodiment equipped with a vent valve 110 that allows passage of gasses but block fluids and solids from passage. The vent valve 110 is according to one embodiment also equipped with a pressure transducer 110. The pressure transducer is used to measure the pressure internally in the chamber 102. By measuring the pressure in the chamber 102 it is ensured that all air or other gases have been evacuated from the chamber 102 prior to the application of the electrical field. To ensure that all air or gas has been pressed out from the chamber 102 prior to the application of the electrical field is very important, this as the field strength that are utilized are so high that they will result in discharges through the air or gas. Discharge through air or gas will result in a hazard as an arch will appear which in turn may lead to an explosion.

According to one embodiment is also possible to use valve V3 as an additive valve, through which an additive in the form of a catalyst or a salt can be added to the pumpable medium.

According to one embodiment an additional valve is mounted in conjunction with the chamber, said valve can be used as an additive valve, through which an additive in the form of a catalyst or a salt that can be added to the pumpable medium.

According to the embodiment shown in FIG. 1 represents the pump casing or cylinder of a piston pump 116 the non-conductive chamber 102. The piston 118 of the piston pump 116 which surface faces the cylinder forms the second electrode plate 108. On the surface of the piston cylinder which is located opposite the piston 118 is the first electrode plate 106 located. In this manner the resulting composite voltage can be applied between the cylinder head and top of the piston, wherein an electrical field will appear over the pumpable medium which is located in the chamber 102. The use of a piston pump 116 enables that the medium under treatment is pressurized, which will result in air or gas in the pumpable medium to be evacuated from the chamber 102 by the vent valve 110.

It should realized that the invention can be exercised also by the use of a pump in which the enclosed chamber and the two electrodes are designed as a flexible insertion located between a moving piston and a fixed wall or a second movable piston with a reversed movement. This could, for example, be a pump similar to that of an infusion bag or a disposable cartridge. In this case, these embodiments, may for example include two metal plates which are placed between two moving walls.

It should also be realized that the invention can be exercised also by the use of other pump types, preferably displacement pumps.

FIG. 2 shows in detail each power supply 100 in an embodiment as shown in FIG. 1. Each power supply 100 consists of several components. A voltage converter T, in this embodiment in the form of a transformer T, supplies the output side of the power supply with a voltage. A diode D is used to rectify the voltage generated by the transformer T. A resistor R adjusts the voltage on the output side. A charge storage device C, in this embodiment in the form of a capacitor C, stores charge when the switch means S1 is in the open position. It is also possible to use several capacitors to adjust the storage capacity, or increase capacity. When the switch means S1 is closed the capacitor is fast discharged and thus a voltage pulse will be generated at the output side 200. The amplitude is adjustable in the range 230-2000 V.

The switch means S1 is controlled by means of a control signal in the form of a current that is applied at 204. The current applied at 204 will in turn control the switch means S1.

According to one embodiment the switch means S1 is a galvanically isolating element.

In one embodiment the switch means is an opto-coupler. By the use of an opto coupler device a very short response time is achieved from the time when current is applied at 204.

The utilize of other types of switches are also possible within the scope of the present invention.

According to the embodiment in FIG. 2 each power supply also include control logic 206 that is provided for a number of internal functions in the power supply. The control logic 206 is part of the control means 104, which provides the control of all the power supplies 100. With the help of control logic 206 can the control means 104 detect if a fault condition is present within each power supply 100. The faults that are detected are component errors, pump errors, voltage present at output 200 of the power supply 100, in the switch means S1, leakage currents in the capacitor C and voltage loss of the transformer T. If a fault is detected by the control logic 206 then the switch means S2 is not closed, which means that the control means 104 detects that this is the case at 208. When the control logic has detected that a fault condition exist then it is no longer possible to control the switch means S1. As an additional safety precaution also the switch means S3 is deactivated by the control logic 206. This means that even if a control signal would be present at 204 of the control means 102 it will not allow switch means S1 to be controlled. The control logic 206 of each power supply 100 detects also if the pressure transducer 110 measures a pressure which is not high enough. This is done by measuring at 210. Also a too low pressure will results in that the switch means S2 will not close and that the switch means S3 is opened.

It should be realized that the same control logic can be used to interrupt an ongoing treatment if faults are detected while the voltage pulse is active.

According to one embodiment the input side of the power supply 202 of transformer T is connected to a supply voltage, preferably a mains voltage in the range 50-500V, more preferred 110-230 V, most preferred 230 V.

It should be realized that is also is possible to exclude the transformer T and directly feed the output side 200 of each power supply 100 with a suitable voltage. It should also be realized that each power supply 100 can be driven from any suitable power source as for example wind power generator and/or solar cells.

In the embodiment shown in FIG. 1 two power supplies 100 are used that are selected from the type shown in FIG. 2. When the pumpable medium is to be exposed to an electric field, by applying a voltage between the electrode plates 106, 108 a serial connection between the two power supplies 100 is created synchronously. This is performed by the control means 104 that generates a control signal which synchronously control the switch organs S1 in the respective individual power supply 100. In this way a resulting composite voltage is generated, which is the sum of the voltage from all the included power supplies 100. By synchronously controlling the switch organs S1 can simple cheap components be used, components that otherwise would be destroyed by the tensions that arise.

In alternative embodiments different number of power supply units 100 are used.

In another embodiment the control means 104 has an arrangement to measure the electrical properties between the first 106 and the second electrode plate 108. The electrical properties that are measured are for example resistance, impedance, capacitance and inductance. By measuring the electrical properties the resulting composite voltage can be adopted to achieve a desired electrical field between the electrode plates 106, 108.

In another embodiment the control means 104 is arranged to apply a resulting composite voltage with a predefined voltage value between the first between the first 106 and the second electrode plate 108. When this is performed the control means 104 simultaneously registers and determines the time constant and amplitude of the voltage and the current of the resulting composite electrical field. The control means 104 then adjusts the resulting composite voltage in order to achieve desired (predetermined) field strength between the first 106 and the second electrode plate 108 when the resulting composite voltage is again applied. Preferably the resulting composite voltage that is utilized to register and determine the time constant and the amplitude for the voltage and current is lower that the resulting composite voltage which is later applied.

In other embodiments several power supplies 100 are used. By allowing the control means 104 to control how many power supplies 100 that are included in the serial connection and thus make a contribution to the resulting composite voltage, the amplitude of the resulting composite voltage can be controlled in a simple manner. By allowing the arrangement to include a larger number of power supplies 100 than what is required to generate a resulting composite voltage of sufficient amplitude, redundancy is achieved. In this manner, the control means 104 disconnects faulty power supplies 100 and connect initially redundant working power supplies 100. In other words, spare power supplies 100 are connected.

Figure 3:
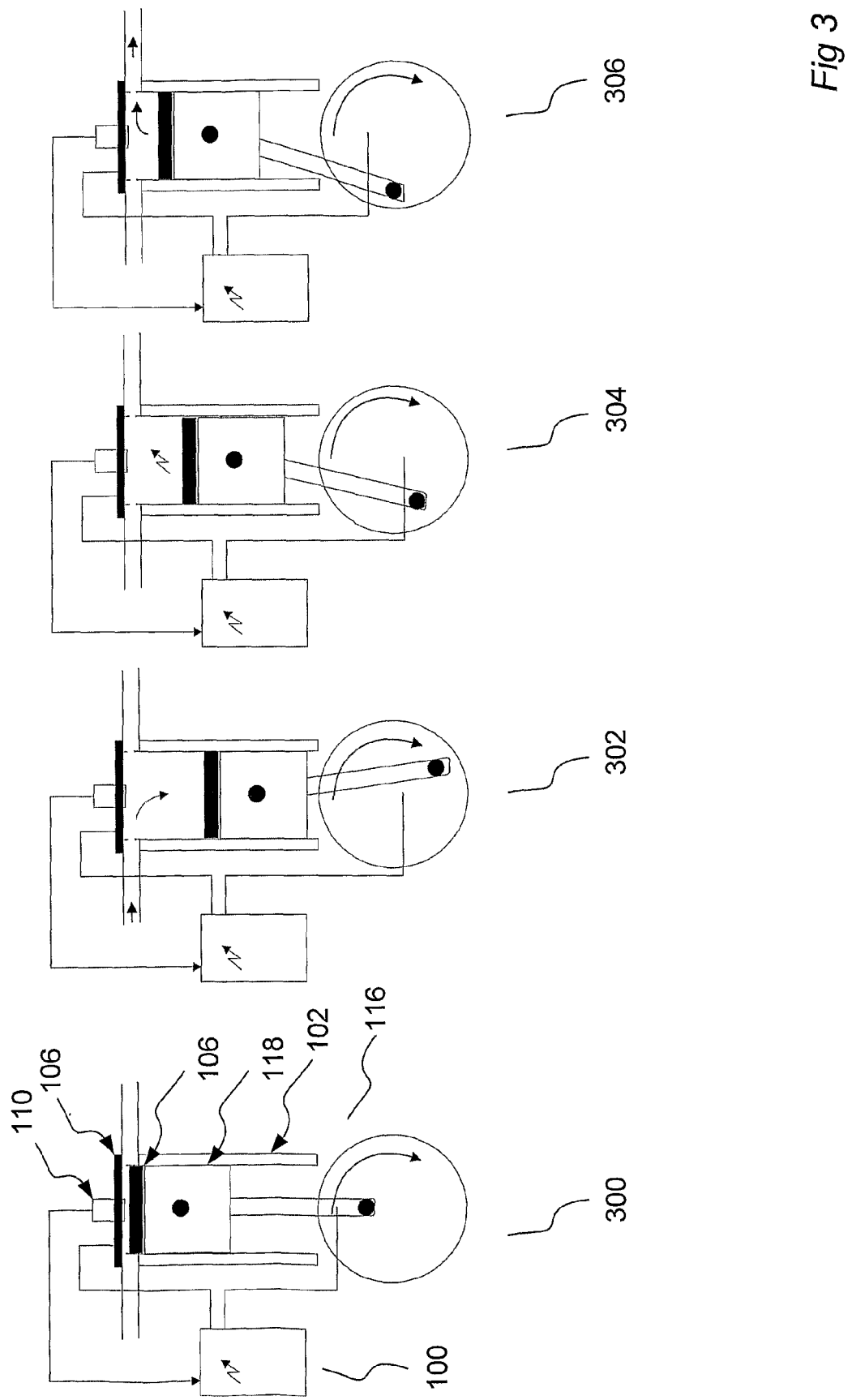
FIG. 3 is a schematic view which shows the working scheme when a system according to an embodiment perform a method to expose a pumpable medium to an electric field.

FIG. 3 schematically shows the operation of an arrangement according to an embodiment when it exposes a pumpable medium to an electric field. Initially the piston pump 116 is in a rest position 300. In this position the input feed and outlet feed valves V1, V2, not shown, are closed.

In the next position 302, according to FIG. 3, the chamber 102 is filled by first opening the input feed valve V1, after which the piston 118 moves downwards. In this manner the pumpable medium is sucked into the chamber 102. When the chamber is full the input feed valve V1 is again closed.

In the next phase 304, according to FIG. 3, the piston 118 moves upwards whereby a pressure builds up in the chamber 102. While the pressure is built up eventual gas and air is pressed out through the vent valve 110.

The vent valve 110 is in accordance with one embodiment equipped with a pressure transducer 110 that registers the pressure in the chamber.

When the pressure has reached a predetermined value this is detected by the control means 104, not shown. At the point when the control means detects a certain pressure, the application of the resulting composite voltage is allowed.

During the filling of the chamber with the pumpable medium has simultaneously an electric voltage been generated by the power supplies 100.

To apply the resulting composite voltage between the electrodes establishes the control means 104, a serial connection between the power supplies 100, the first 106 and the second electrode plate 108, wherein the resulting composite voltage will expose the pumpable medium to an electric field.

According to one embodiment the resulting voltage can be applied a desired number of times to achieve a desired treatment of the pumpable medium.

In the next step 306, according to FIG. 3, the outlet feed valve V2 is opened after which the piston 118 moves upwards. In this manner the chamber is again emptied from the pumpable medium.

The procedure is thereafter again repeated if it is desired to treat more pumpable medium.

Figure 4:
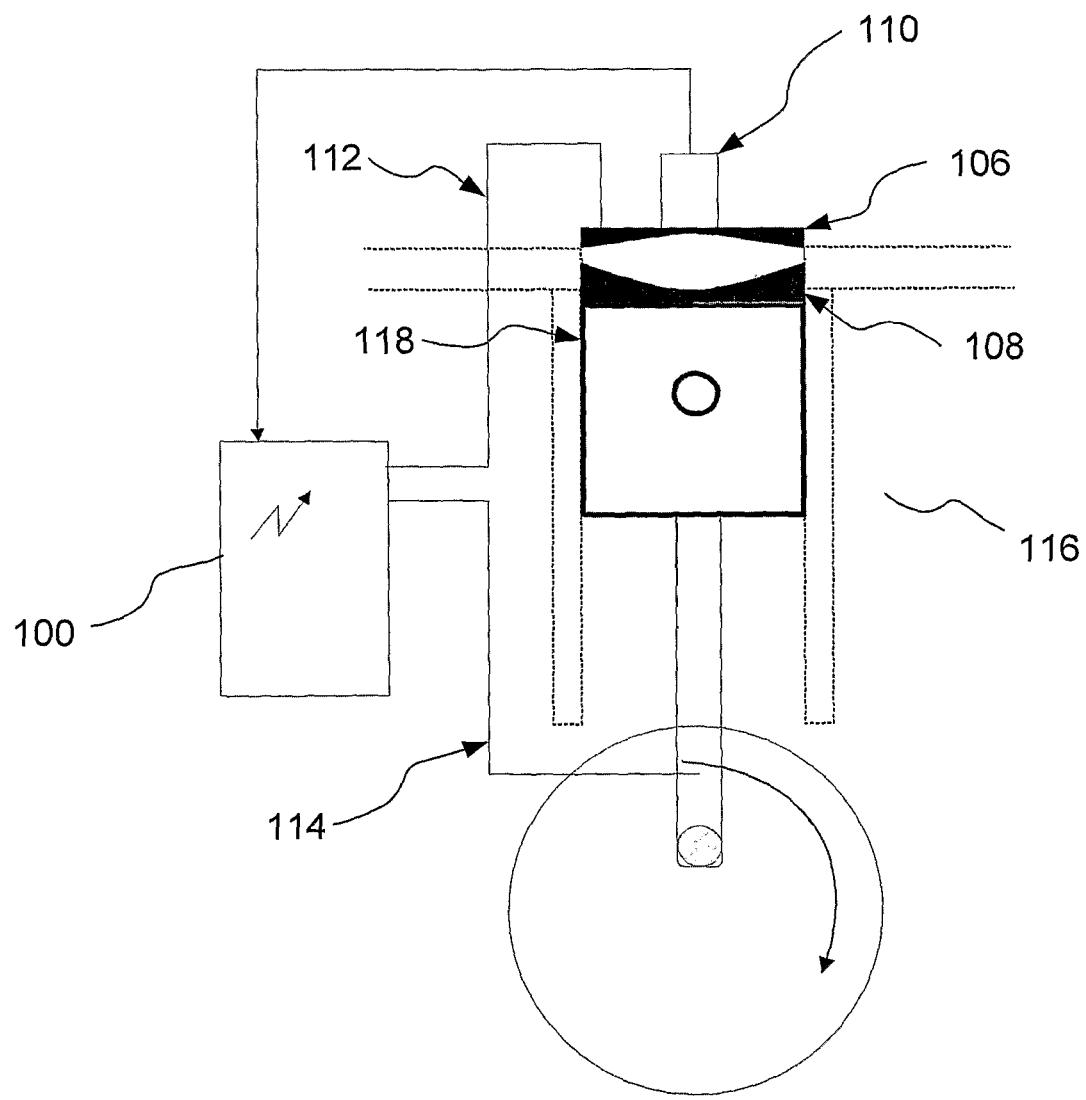
FIG. 4 is a schematic view showing how a chamber is equipped with electrodes with varying distances, according to an embodiment.

FIG. 4 shows an alternative embodiment in which the first electrode plate 106 and the second electrode plate 108 are designed in such a way that the distance between the first electrode plate 106 and the second electrode plate 108 is less further from the centre point of the chamber 102 than that closer centre point. By designing the electrodes 106, 108 in this manner it is compensated for the peripheral effects of the electric field that appear due to the geometric design of the electrodes 106, 108. By doing so a uniform electric field across the chamber 102 is obtained.

In another embodiment the first electrode plate 106 and second electrode plate 108 are provided with non-conducting areas that are wider closer to the centre point of the chamber 102 than further away from the centre point. In this way, it is possible to compensate for the peripheral effects that occur and thus obtain an uniform electric field.

In alternative embodiment of the present invention can be of several chambers 102 be used to pump the pumpable medium. In this manner, it is possible to increase the capacity of the arrangement without having to design larger pump units. Also in this case it is possible to use both piston pumps 116 as well as other pump types, preferably displacement pumps.

Another advantage that is achieved by the use of multiple chambers is that a continuous flow through the arrangement can be achieved. To achieve this, according to one embodiment the pumps are organised in such a manner that at least one chamber 102 is always filled with the pumpable medium and one chamber is always emptied form the pumpable medium. In the case where piston pumps 116 are used, this is achieved for example by arranging the piston pumps 116 pistons on a common crankshaft, similar to that of pistons in a multi-cylinder internal combustion engine.

Other solutions are of course also possible without departing from the scope of present invention. For example, the type described above for an infusion bag or a disposable cartridge are fully possible.

In order to effectively use multiple chambers 102 a distribution means is used according to one embodiment that distributes the pumpable medium between the respective chambers. For example, one or more multi-way valves used to distribute the pumpable medium between the respective chambers 102. Also other distribution organs can be utilized.

The present invention is suitable for use on various pumpable media in which there is a risk that there are unhealthy microorganisms.

The present invention is well suited to the clean water of the most varying qualities. When hazardous water or contaminated water from various processes must be purified, the invention is adequate to neutralize microorganisms. Also when water is pumped in and out from ballast tanks of ships, or between ballast water tanks on the ship during a voyage, it is appropriate to use the invention to prevent contamination and/or foreign aquatic species spread to be across oceans and waters. Similarly, the invention is suitable for exposing humidification water, irrigation water or drinking water for an electric field. Thus, to an embodiment is provided to expose hazardous water, ballast water, pool water, pond water, contaminated water, humidification water, drinking water and/or waste water to an electric field.

Also when the air or products that are susceptible to dehydration is humidified it is appropriate to use the present invention to prevent water-borne infections such as Legionella to be spread through the humidification installation. Similarly, the invention prevent Legionella spread through the hot water network by exposing the hot water to an electric field. Also when the water in a pool or basin is to be purified the present invention is suitable for use. Also drinking water and waste water can be purified with the invention. The invention may for example be part of a mobile water purification plant. This means that the invention can be used when a temporary water treatment capacity is needed, such as in refugee camps. An embodiment of the present invention is therefore to be installed in conjunction to a mobile water purification plant, a hot water supply tank, a humidification plant, a pool or a basin.

When water is to be purified it is suitable to combine the invention with other water purification techniques such as UV, ozone or vortex treatment. Therefore, an embodiment is provided that is combined with at least one treatment that is selected from the group consisting of but not limited to UV, ozone and vortex treatment to purify water.

Another appropriate use of the present invention is the purification of suspended products, such as soil suspensions. Therefore an embodiment is provided to expose a suspension of product to an electric field.

Another area for use is within the food industry, where the present invention can be used instead of or in addition to conventional pasteurization methods. When the present invention is used there is no need the food in question to be heated, which allows the taste, appearance and texture of the food to be maintained. Furthermore, energy savings are large when the food does not require to be heated. Thus an embodiment is provided to expose a pumpable foodstuff to an electric field.

Another area for use is for biogas production, where the present invention can be used instead of or in addition to the conventional treatment for biological purification of a sludge. When the present invention is used, the fermentation process can be properly controlled as non-desired bacteria in the sludge is neutralized or killed efficiently. Furthermore, energy savings are large as the sludge material do not require to be heated. The present invention thus provides an embodiment for the exposure of a sludge to an electric field.

Furthermore, the present invention is well suited for the sterilisation of pumpable pharmaceuticals and/or pumpable raw materials for the manufacture of pharmaceuticals. In view of this, one embodiment is provided for the exposure of a pumpable pharmaceutical and/or a pumpable raw material for the manufacture of pharmaceuticals to an electric field.

It should recognized that the man skilled in the art can adapt the above described embodiments in many ways and still use the advantages of the invention described in the embodiments above. Therefore should not this invention be limited to the scope of the described embodiments but only defined by the attached patent claims.

The invention claimed is:

1. An arrangement for the exposure of a pumpable medium to an electric field, wherein the arrangement comprises:
   power supply for the generation of electrical voltage,
   at least one non-conducting chamber for pumping said pumpable medium, which said at least one chamber is provided with a first and a second electrode plate,
   wherein the power supply comprises at least two power supplies for the generation of an electrical voltage, wherein each power supply comprises a voltage converter (T), an electric charge storing element (C), and a switch (S1);
   a control means for controlling said at least two power supplies, wherein the control means by synchronous control of each power supply switch (S1) with a common control signal, generated by the control means in the form of a pulse with a duration of 0.1-100 microseconds, establish a serial connection between at least two of said at least two power supplies, the first electrode plate and the second electrode plate, wherein a resulting composite voltage arises between the first and the second electrode plate, which resulting composite voltage creates an electric field between the first and the second electrode plate, wherein the pumpable medium is exposed to the electric field, and
   wherein said at least one non-conducting chamber for pumping said pumpable medium is a piston pump with a piston whose top surface is one of the electrode plates, wherein the piston pump is connected to an input feed pipe and an outlet feed pipe.

2. The arrangement according to claim 1, wherein said chamber for pumping said pumpable medium is a pump designed as a flexible chamber which comprises the first electrode plate and second electrode plate, which is located between a moving piston and a stationary wall or between two moving pistons working in reversed phase.

3. The arrangement according to claim 2, wherein the flexible chamber is an infusion bag or a disposable cartridge.

4. The arrangement according to claim 1, wherein the voltage converter (T) is a transformer.

5. The arrangement according to claim 1, wherein the electric (previously presented) charge storing element (C) is at least one capacitor.

6. The arrangement according to claim 1, wherein the switch (S1) is a galvanically isolating element.

7. The arrangement according to claim 1, wherein the switch (S1) is an optical coupler.

8. The arrangement according to claim 1, wherein the control means controls how many of said at least two power supplies that shall be connected in series and thus contributes to the resulting composite voltage.

9. The arrangement according to claim 1, wherein the inlet feed pipe is equipped with an inlet feed valve (V1) and/or the outlet feed pipe is equipped with and outlet valve (V2).

10. The arrangement according to claim 1, wherein said at least one chamber is equipped with a valve which allows passage of gas phase media but blocks passage of fluid or solid media.

11. The arrangement according to claim 1, wherein said at least one chamber is equipped with a pressure transducer, wherein said control means performs the serial connection of said at least two power supplies when a predefined pressure has been sensed by the pressure transducer.

12. The arrangement according to claim 1, wherein said at least one chamber is equipped with a drain connection and a drain valve (V3).

13. The arrangement according to claim 1, wherein said at least one non-conducting chamber or the inlet feed pipe and/or the outlet feed pipe is equipped/are equipped with an additive connection and an additive valve.

14. The arrangement according to claim 1, wherein the distance between the first electrode plate and the second electrode plate is shorter further away from a centre point of the at least one non-conducting chamber than closer to said centre point.

15. The arrangement according to claim 1, wherein the first electrode plate and/or the second electrode plate comprises non-conducting areas, where said non-conducting areas are wider closer to a centre point of the at least one non-conducting chamber than further away from said centre point.

16. The arrangement according to claim 15, further equipped with a distribution means which controls an inlet pumping and an outlet pumping of the pumpable medium in each of the at least one non-conducting chamber.

17. The arrangement according to claim 1, wherein said at least one non-conducting chamber is a piston pump which is connected in parallel with at least one other non-conducting chamber which also is a piston pump.

18. A method for the exposure of a pumpable medium to an electric field,
comprising the steps of;
that at least one non-conducting chamber, which is equipped with a first and a second electrode plate and which consists of a piston pump with a piston, whose upper part is one of the electrode plates, wherein the piston pump is connected to an inlet feed pipe and an outlet feed pipe, is filled with the pumpable medium, wherein the pumpable medium is subjected to a pressure;
that an electrical voltage is generated by at least two power supplies, wherein each power supply comprises a voltage converter (T), an electrical charging storage element (C), and a switch (S1);
that a control means for controlling said at least two power supplies by synchronous control of each power supply switch (S1) with a common control signal, generated by the control means in the form of a pulse with a duration of 0.1-100 microseconds, establishes a serial connection between at least two of said at least two power supplies, the first electrode plate and the second electrode plate, wherein a resulting composite voltage arises between the first and the second electrode plate, which resulting composite voltage results in the electric field between the first and the second electrode plate, wherein the pumpable medium is exposed to the electric field, and
that said at least one non-conducting chamber is emptied from the pumpable medium.

19. The method according to claim 18, wherein the steps to generate an electrical voltage and to establish a serial connection is performed a number of times in said order.

20. The method according to claim 18, wherein the step of emptying said at least one non-conducting chamber from the pumpable medium further comprises a step of feeding said pumpable medium through a drain valve (V3).

21. The method according to claim 18, wherein said at least one non-conducting chamber in the form of a piston pump is connected in parallel with at least one other similar non-conducting chamber and where a distributing means controls the inlet pumping and outlet pumping of the pumpable medium in each of the non-conducting chambers in a manner so that at least one non-conducting chamber is always filled with the pumpable medium and at least one non-conducting chamber is always emptied from the pumpable medium.

22. The method according to claim 18, wherein the pumpable medium has a risk for unhealthy microorganisms.

23. The method according to claim 18, wherein the pumpable medium is a pumpable food stuff.

24. The method according to claim 18, wherein the pumpable medium is a hazardous water, ballast water, pool water, pond water, contaminated water, humidification water, drinking water and/or waste water.

25. The method according to claim 18, wherein the pumpable medium is a suspended product.

26. The method according to claim 18, wherein the pumpable medium is a commodity or raw material that is aimed for biogas production.

27. The method according to claim 18, wherein the pumpable medium is a petroleum product.

28. The method according to claim 18, wherein the pumpable medium is at least one selected from the group consisting of pumpable drugs, pumpable commodity and raw material for the manufacture of pharmaceuticals.

29. The method according to claim 18, wherein the pumpable medium is from a mobile water purification plant, a hot water supply tank, a humidification plant, a pool and a basin.

30. The method according to claim 18, further comprising at least one treatment chosen from the group consisting of ultra violet, ozone and vortex treatment.

31. The method according to claim 18, wherein the duration of the pulse is 1-100 microseconds.

32. The method according to claim 18, wherein the field strength of the electric field between the first and the second electrode plate is in the range of 1-30 kV/cm.

33. The method according to claim 18, wherein each of the at least two power supplies provides the electrical voltage as an adjustable electrical voltage in the range of 230-2000 volts.

34. The method according to claim 18, wherein the control means is arranged to generate the pulse repeatedly with a frequency of 1 Hz-100 kHz.

35. The method according to claim 18, wherein the control means detects fault conditions in each of the at least two power supplies before and/or during the serial connection is established, wherein said fault conditions are selected from the group consisting of component errors, pump errors, voltage at an output of each of the at least two power supplies, short circuit in said switch (S1), leakage currents in said electric charge storage element (C) and voltage loss in said voltage converter (T).

36. The method according to claim 18, wherein the control means measures electrical properties, between the first and the second electrode plate, including, but not limited to, resistance, impedance, capacitance and inductance, and adjusts the resulting composite voltage so that a predefined field strength is achieved between the first and the second electrode plate.

37. The method according to claim 18, wherein the control means applies the resulting composite voltage with a predefined value between the first and the second electrode plate and measures a time constant of the pulse and an amplitude of the voltage and a current in the resulting field, whereafter the control means adjusts the resulting composite voltage so that a predefined field strength is achieved between the first and the second electrode plate, when a resulting composite voltage again is applied.

* * * * *